(12) United States Patent
Kunkle (10) Patent No.: US 11,877,936 B2
(45) Date of Patent: Jan. 23, 2024

(54) FACET FUSION TUBE ASSEMBLY

(71) Applicant: William Aaron Kunkle, Ft. Wayne, IN (US)

(72) Inventor: William Aaron Kunkle, Ft. Wayne, IN (US)

(*) Notice: Subject to any disclaimer, the term of this patent is extended or adjusted under 35 U.S.C. 154(b) by 6 days.

(21) Appl. No.: 17/450,715

(22) Filed: Oct. 13, 2021

(65) Prior Publication Data

US 2022/0151804 A1    May 19, 2022

Related U.S. Application Data

(60) Provisional application No. 63/113,229, filed on Nov. 13, 2020.

(51) Int. Cl.
*A61F 2/46*    (2006.01)
*A61F 2/44*    (2006.01)
A61F 2/30     (2006.01)

(52) U.S. Cl.
CPC .......... *A61F 2/4611* (2013.01); *A61F 2/4405* (2013.01); *A61F 2/4455* (2013.01); *A61F 2002/30069* (2013.01); *A61F 2002/30235* (2013.01); *A61F 2002/30329* (2013.01); *A61F 2002/4687* (2013.01)

(58) Field of Classification Search
CPC .. A61F 2/46; A61F 2002/4687; A61F 2/4405; A61F 2/4455; A61F 2/4601; A61F 2/4611; A61B 17/1757; A61B 17/46; A61B 17/90; A61B 17/8805; Y10T 403/7176
USPC ........................................................ 403/397
See application file for complete search history.

(56) References Cited

U.S. PATENT DOCUMENTS

| | | | | |
|---|---|---|---|---|
| 6,071,233 A | * | 6/2000 | Ishikawa | A61B 1/0014 600/129 |
| 6,408,492 B1 | * | 6/2002 | Sparks | A01K 97/08 24/336 |
| 8,727,967 B2 | * | 5/2014 | Weitzner | A61B 1/018 396/17 |
| 2005/0234297 A1 | * | 10/2005 | Devierre | A61B 1/00087 600/129 |
| 2009/0149857 A1 | * | 6/2009 | Culbert | A61B 1/0684 606/191 |

(Continued)

FOREIGN PATENT DOCUMENTS

WO    WO-2020261203 A1 * 12/2020 ......... A61B 17/1671

*Primary Examiner* — Jan Christopher L Merene
*Assistant Examiner* — Anna V. Little
(74) *Attorney, Agent, or Firm* — Maginot, Moore & Beck LLP (57) ABSTRACT

A facet fusion tube assembly includes an elongated tube that defines a working channel to accept tools, instruments or materials for conducting a facet fusion. The tube includes a clip on its outer circumference that is configured to engage the outer surface of an adjacent tool or instrument used to access and engage the pedicle. A centering cap can be mounted at the proximal end of the elongated tube to align and center a working tool, such as a burring tool. An inner removable rod can extend through the tube to prevent soft tissue migration into the tube during insertion, and can be used for bone graft packing once the facet joint or other area of the spine is prepared for fusion. In use, the tube is clipped onto an adjacent instrument or tool to anchor the facet fusion tube assembly in a proper orientation relative to the facet joint.

16 Claims, 7 Drawing Sheets

(56) References Cited

U.S. PATENT DOCUMENTS

| | | | |
|---|---|---|---|
| 2011/0108150 A1* | 5/2011 | Renaud | F02M 35/10144 24/457 |
| 2014/0025121 A1* | 1/2014 | Foley | A61B 17/3421 606/279 |
| 2014/0277467 A1* | 9/2014 | Hibri | A61F 2/44 623/17.12 |
| 2015/0342649 A1* | 12/2015 | McCormack | A61B 17/1671 606/279 |
| 2015/0374354 A1* | 12/2015 | Boyd | A61B 17/1757 600/204 |
| 2018/0153592 A1* | 6/2018 | Larson | A61B 17/7074 |
| 2018/0271602 A1* | 9/2018 | Frey | A61F 2/30942 |
| 2018/0318034 A1* | 11/2018 | Julian Ibañez | A61B 90/361 |
| 2019/0083271 A1* | 3/2019 | Donner | A61B 17/1739 |

* cited by examiner

FACET FUSION TUBE ASSEMBLY

PRIORITY CLAIM

This application is a utility filing from and claims priority to U.S. Provisional Application No. 63/113,229, filed on Nov. 13, 2020, the entire disclosure of which is expressly incorporated herein by reference.

BACKGROUND

The present invention relates to the field of minimally invasive spine surgery and more particularly to instruments and methods for reliable and enhanced access to the facet joints.

There are numerous devices to allow for minimally invasive access to the posterior spine. Examples of devices designed for minimal access to the posterior spine are disclosed in U.S. Pat. No. 7,226,451 ('451 patent), issued on Jun. 5, 2007, and U.S. Pat. No. 7,736,305 ('305 patent), issued on Jun. 15, 2010. The devices disclosed in these patents are geared toward access for pedicle screw insertion, for rod or plate connection with the pedicle screws, and for access and insertion of biomechanical interbody implants for fusion. These devices do not specifically address the requirements for facet fusion or provide a specific technique or device for facet fusion. U.S. Pat. No. 7,935,136 ('136 patent), which issued on May 3, 2011, describes a specific type of tether to wrap around the superior and inferior articular process that form a facet joint, as well as an aid in fusion.

The devices in '451 and '305 patents utilize a minimally invasive tube to access the posterior spine, but the purpose of these devices is to allow for easier access to pedicle screws, rod insertion and assembly and access to the interbody space to allow of insertion of an interbody fusion device. The device in the '136 patent attempts to address a technique to enhance facet fusion with a tether device but does not do it in a minimally invasive way. The device of the '136 patent still requires open surgical techniques that necessarily require stripping of significant paraspinal muscle, which can potentially lead to delayed surgical recovery, muscle necrosis, increased blood loss and morbidity.

U.S. Application No. 2013/0253591 ('591 Publication), published on Sep. 26, 2013, discloses a device designed for minimally invasive spine fusion, in particular a longitudinally-directed tube in a cephalad to caudal orientation with split in the tube. The tube in the '591 Publication does not allow for complete decortication or access to the facet joint because it is not configured to allow access for a high-speed burr or drill directly (in a posterior to anterior orientation) onto the facet joint. The device in '591 Publication does not ensure reliable access to the facet joint via direct association to a pedicle cannulation device. In addition, this device targets a posterolateral area for spine fusion with decortication of the transverse process.

There is a need for an apparatus and techniques that overcome the disadvantages of the prior systems discussed above.

SUMMARY OF THE DISCLOSURE

A facet fusion tube assembly includes an elongated tube of a length sufficient to provide access to the facet joint of any vertebral level. The tube is hollow and open at both ends to operate as a working channel to accept tools, instruments or materials for conducting a facet fusion. The tube includes a clip that is mounted to the outer circumference of the tube and that is configured to engage the outer surface of an adjacent tool or instrument, particularly tools or instruments used to access and engage the pedicle. In one feature, the tube assembly is provided with a centering cap that can be mounted at the distal end of the elongated tube to align and center a working tool, such as a burring tool. In another feature, an inner removable rod extends through the tube to prevent soft tissue migration into the tube during insertion, and to be used for bone graft packing once the facet joint or other area of the spine is prepared for fusion.

Once a pedicle is cannulated, accessed in any manner or a bone screw is inserted percutaneously, the tube of the facet fusion tube assembly can be clipped onto the associated instrument or tool. In one approach, the tube is passed down along the tool/instrument until the distal end of the tube is positioned directly over the facet capsule and joint, consisting of the superior and inferior articular process of a motion segment. Once the tube is positioned over the facet joint a high-speed burr can be placed down the tube with the centering cap so that the facet joint can be reliably and accurately decorticated and prepared for fusion. Once the facet joint has been decorticated, the tube can then be used to pass morselized allograft, autograft or any FDA approved bone graft material directly into the facet joint and packed in place with the inner rod device passed down the tube.

DETAILED DESCRIPTION

Various embodiments and aspects of the inventions will be described with reference to details discussed below, and the accompanying drawings will illustrate the various embodiments. The following description and drawings are illustrative of the invention and are not to be construed as limiting the invention. Numerous specific details are described to provide a thorough understanding of various embodiments of the present invention. However, in certain instances, well-known or conventional details are not described in order to provide a concise discussion of embodiments of the present inventions.

Figures 1, 2:
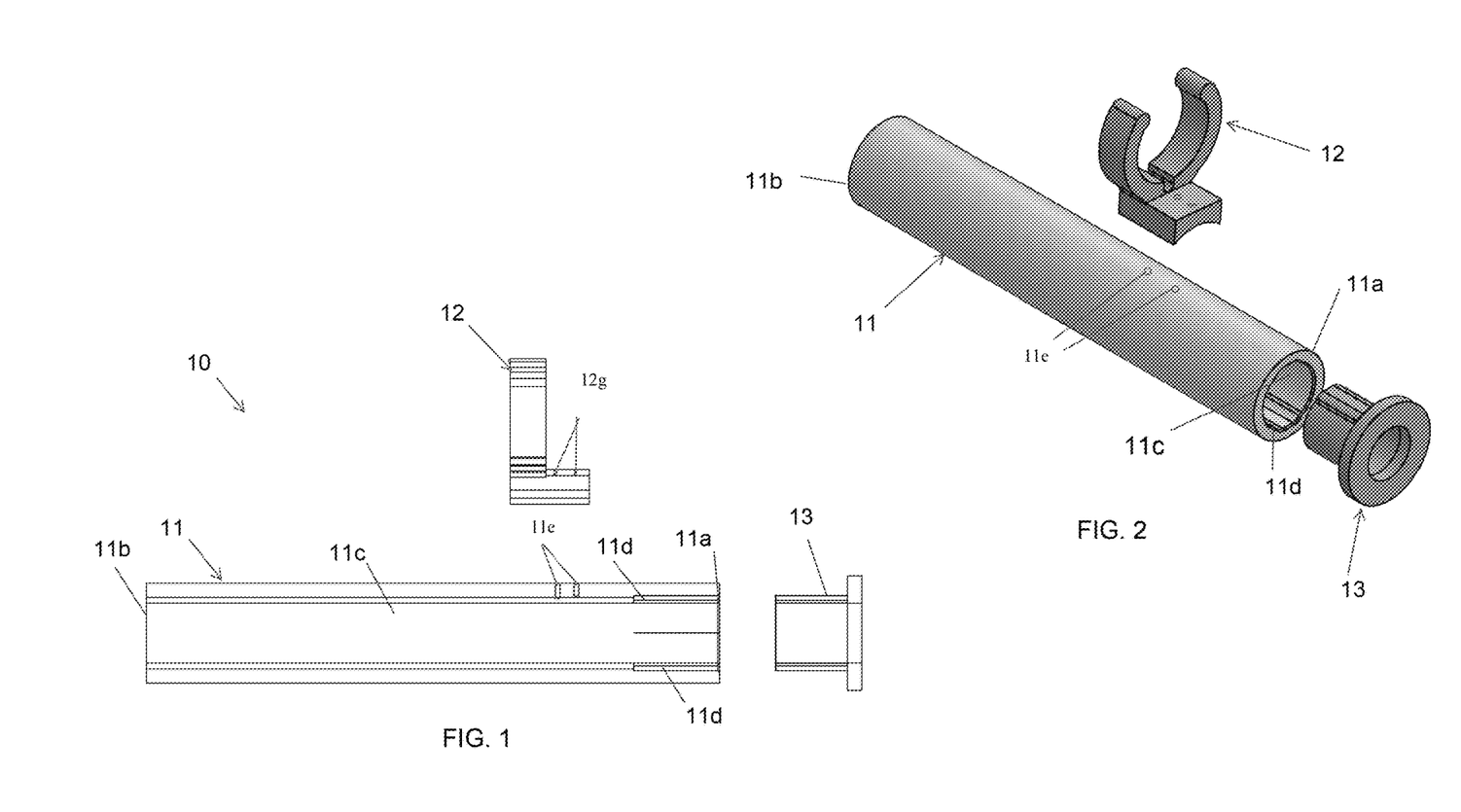
FIG. 1 is an exploded, partial cross-section, view of a facet fusion tube assembly according to the present disclosure.
FIG. 2 is a perspective view of the facet fusion tube assembly shown in FIG. 1.
Figure 3A:
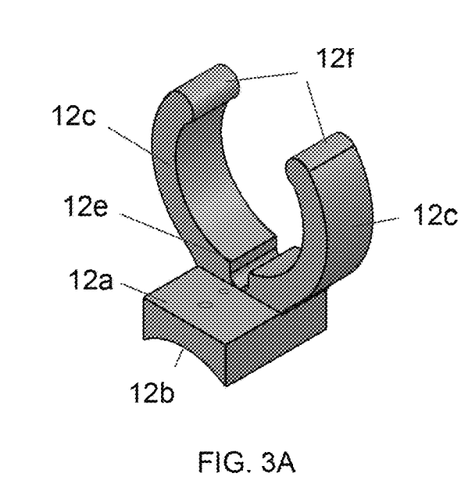
FIGS. 3A-3D are perspective, end, side and top views of a clip of the facet fusion tube assembly shown in FIG. 1.
Figure 3B:
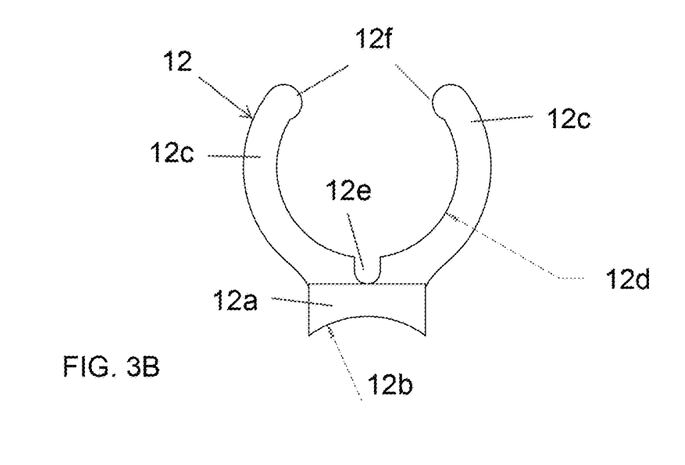
Figure 3C:
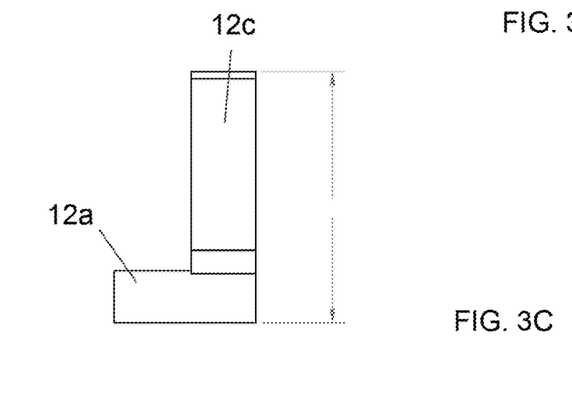
Figure 3D:
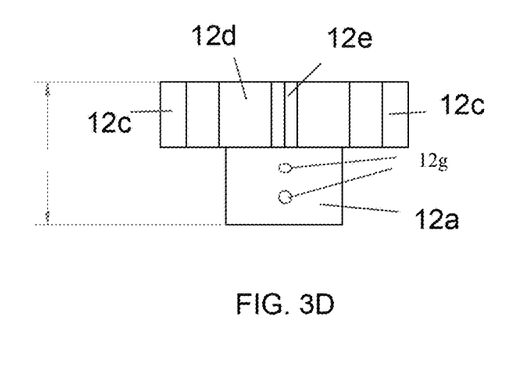
Figure 4A:
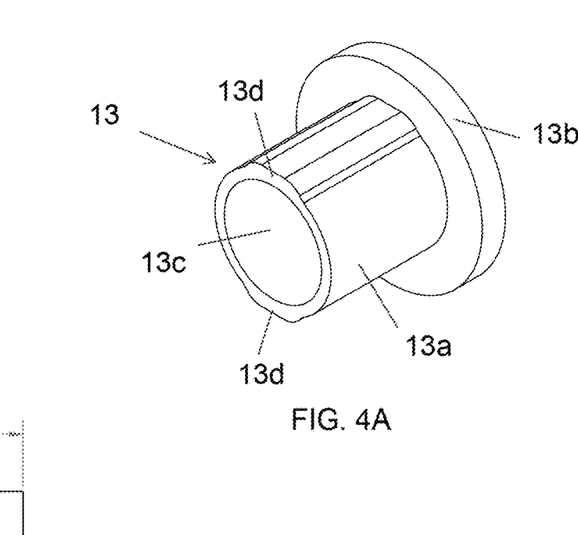
FIGS. 4A-4D are perspective, end, side and top views of a centering cap of the facet fusion tube assembly shown in FIG. 1.
Figures 4B, 4D:
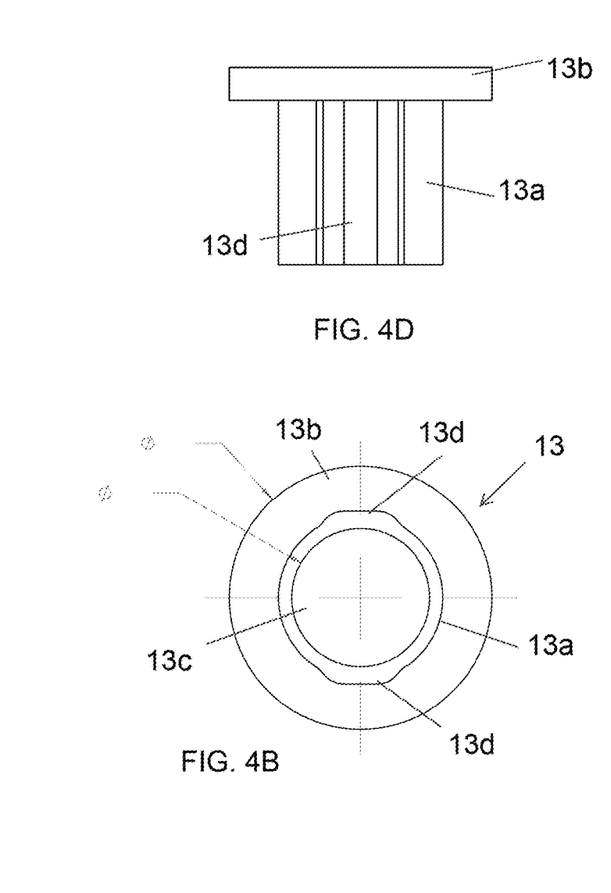
Figure 4C:
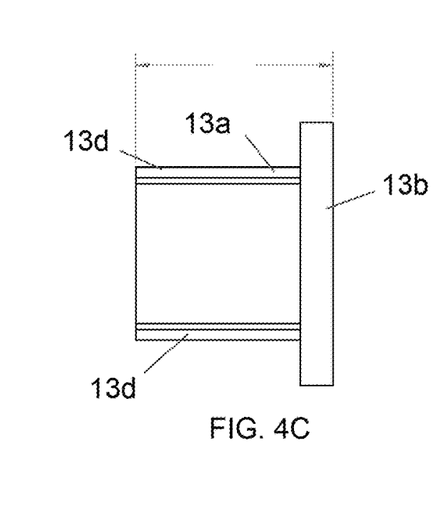

In one aspect of the present disclosure, a facet fusion tube assembly 10 includes a tube 11 and an attachment clip 12, as shown in FIGS. 1-2. The tube 11 is sized for percutaneous introduction into a spinal level with the 11a of the tube accessible outside the patient's body and the distal end 11b adjacent the facet joint at the spinal level. The tube 11 defines a central bore 11c from the proximal to the distal end that is sized to receive instruments and biomaterials for fusion of the facet joint. In one specific embodiment, the tube 11 can have a length between the ends 11a, 11b of 80 mm and an inner diameter of the bore 11c of 10 mm.

The attachment clip 12, as shown in FIGS. 3A-3D, includes a base 12a with a curved surface 12b sized to conform to the outer diameter of the tube 11. A pair of opposing arms 12c project from the base 12a and define a generally cylindrical interior engagement surface 12d. The arms 12c are configured to flex outward relative to each other to accept a tool or instrument introduced into the engagement surface 12d. A central notch 12e can be provided to facilitate the outward flexing of the arms. A knob 12f can be provided at the free end of the arms to facilitate expansion of the arms as an instrument is introduced into the gap between the knobs. The knobs 12f can also help to retain the tool/instrument within the engagement surface 12d of the clip.

In one embodiment, the base 12a of the clip can have a length of 10 mm, with the arms 12c extending 20 mm from the surface 12b of the base, and thus 20 mm from the surface of the tube 11. The engagement surface 12d can be defined at an effective radius of 7.0 mm so that the clip can clamp onto or engage a tool or instrument having an effective diameter of 14-15 mm. Of course, other dimensions are contemplated that allow the clip 12 to engage the tool or instrument, and particularly that allow the arms 12c to solidly engage the tool/instrument with sufficient force to prevent disengagement of the clip from the tool/instrument.

The clip 12 can be attached to the tube 11 at any location along the length of the tube. The attachment is preferably a permanent attachment, such as by welding the base 12a to the tube. Alternatively, the clip 12 can be removably, but rigidly, connected to the tube by passing one or more conventional fasteners through holes 11e and 12g in the tube and the clip base, respectively. In another alternative, the tube can be provided with a series of fastener holes, such as the holes 11e, along the length of the tube to align with the holes 12g in the base 12a to receive the conventional fasteners. The series of holes allow selection of the location of the clip along the length of the tube. Preferably, two sets of holes are provided—one nearer the distal end 11a of the tube, as depicted in FIGS. 7-8, and the other nearer the proximal end 11b of the tube, as depicted in FIGS. 1-2.

In one embodiment, the tube assembly includes a centering cap 13, shown in FIGS. 4A-4D, that is pressed into the proximal end 11a of the tube (FIGS. 1-2). The cap 13 includes a cylindrical body 13a that is sized for press-fit or friction-fit engagement within the central bore 11c of the tube 11. A plate 13b at the end of the body engages the end of the tube to fix the position of the centering cap within the tube. The body and cap define a centering bore 13c that is sized to accept tools and instruments for performing a facet fusion. To enhance the engagement and to prevent rotation of the cap relative to the tube, the cylindrical body includes a pair of ridges 13d. The proximal end 11a of the bore 11c includes opposing cut-outs or channels 11d that extend a fixed depth into the tube 11 (FIGS. 1-2). The channels 11d are sized and arranged to receive the ridges 13d in nested arrangement when the centering cap is pressed into the tube. In one specific embodiment, the channels 11d are defined at a width between the channels of 4 mm with a depth of 0.67 mm. The cylindrical body 13a of the cap has outer dimensions that substantially match the inner diameter of the central bore 11c and the width of the channels 11d. The plate 13b can have a diameter that is slightly larger than the outer diameter of the tube, such as 14 mm in one specific embodiment. The cylindrical body 13a can have a length of 10 mm, with the depth of the channels 14d being slightly longer than the body of the centering cap. The centering bore 13c has an inner diameter to accept conventional tools and instruments for performing a facet fusion, such as a high-speed burring tool. In a specific embodiment, the inner diameter can be 8.5 mm.

Figures 5, 6:
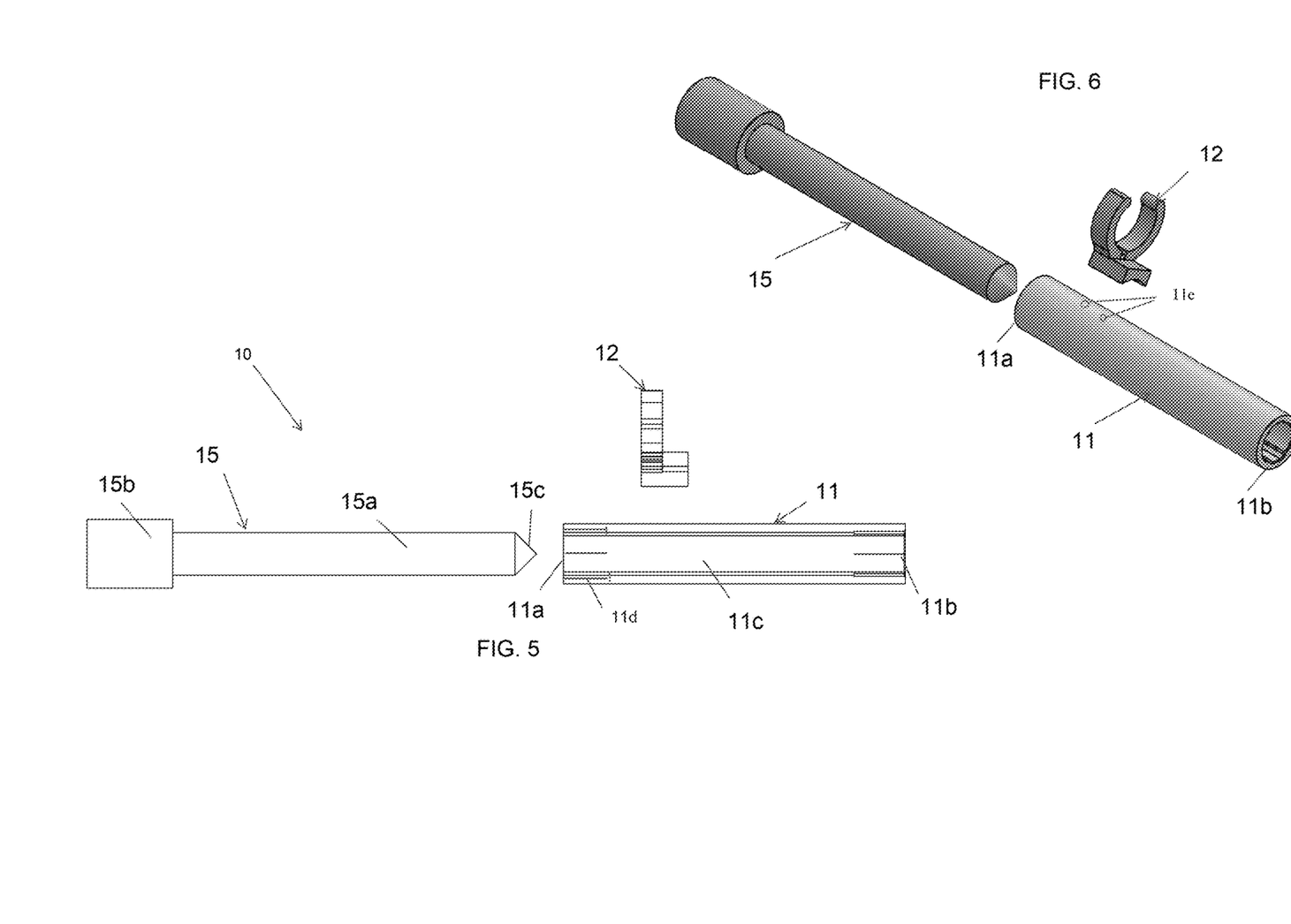
FIG. 5 is an exploded, partial cross-section, view of the clip and tube of the facet fusion tube assembly shown in FIG. 1, together with an inner rod disposed within the tube, according to one embodiment of the present disclosure.
FIG. 6 is a perspective view of the clip, tube and inner rod shown in FIG. 5.

In the illustrated embodiment, a single centering cap 13 is provided at the proximal end 11a of the tube. Alternatively, the centering cap can be provided at the distal end 11b, or a centering cap can be provided at both ends of the tube. In the latter case, channels 11d would be incorporated into the tube 11 at the distal end 11b, as depicted in FIG. 5. However, in the preferred embodiment, the centering cap is only engaged at the proximal end so that the cap can be added to a tube 11 that is already in place within the patient's body, as described herein.

Figures 7, 8:
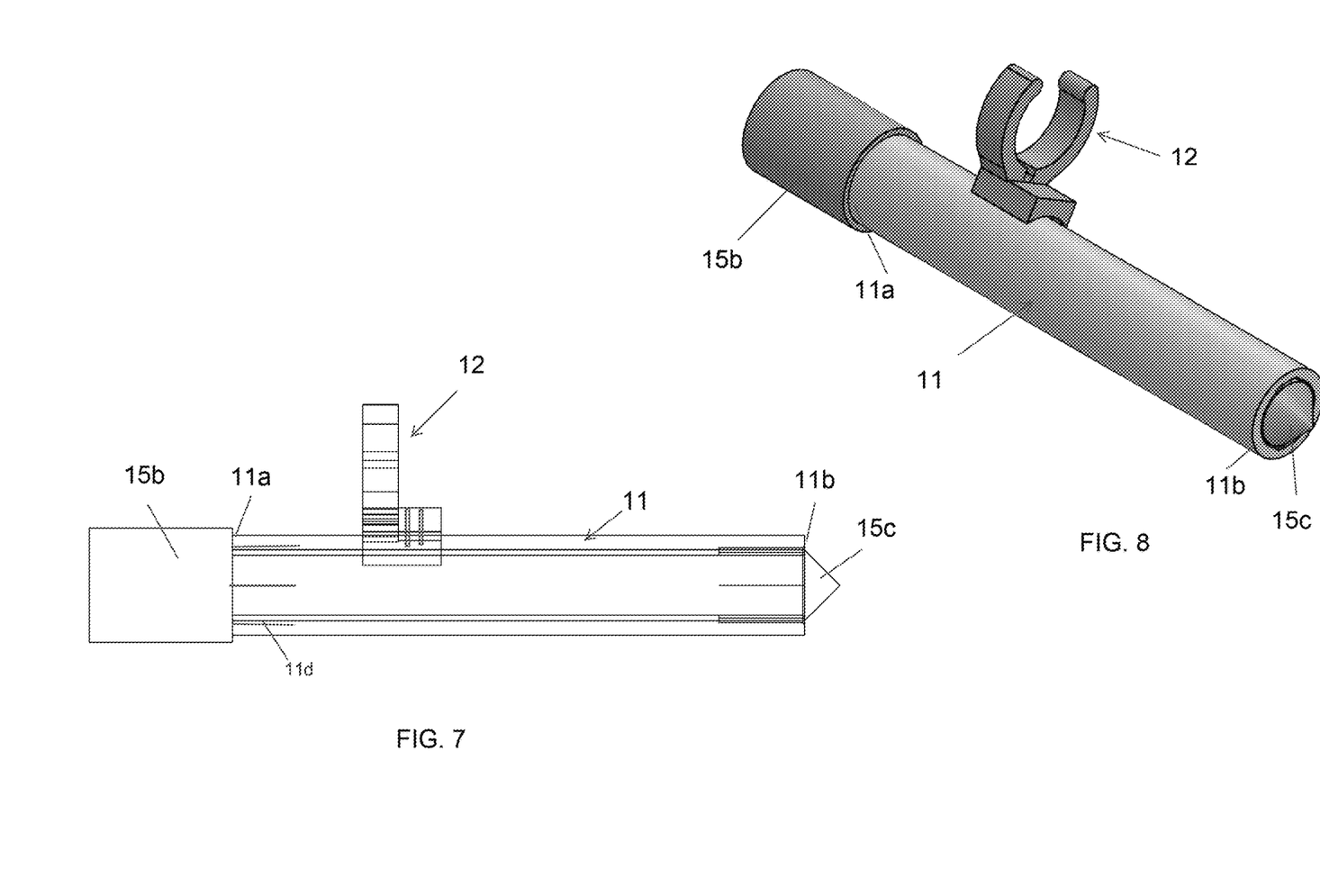
FIG. 7 is a side cross-sectional view of the clip, tube and inner rod of FIG. 5, shown in an assembled configuration.
FIG. 8 is a perspective view of the assembled configuration shown in FIG. 7.
Figure 9A:
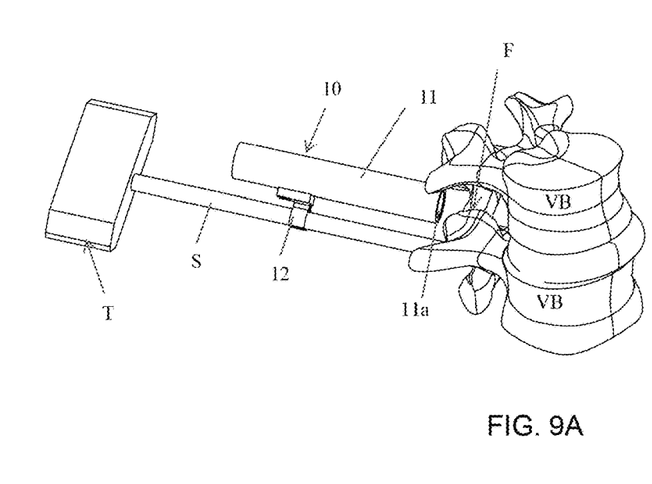
FIGS. 9A-9D are perspective, sagittal, coronal and axial views of a lumbar spinal segment with the tube assembly of FIG. 1 aligned over a facet joint and supporting on a tool for accessing the pedicle.
Figures 9B, 9D:
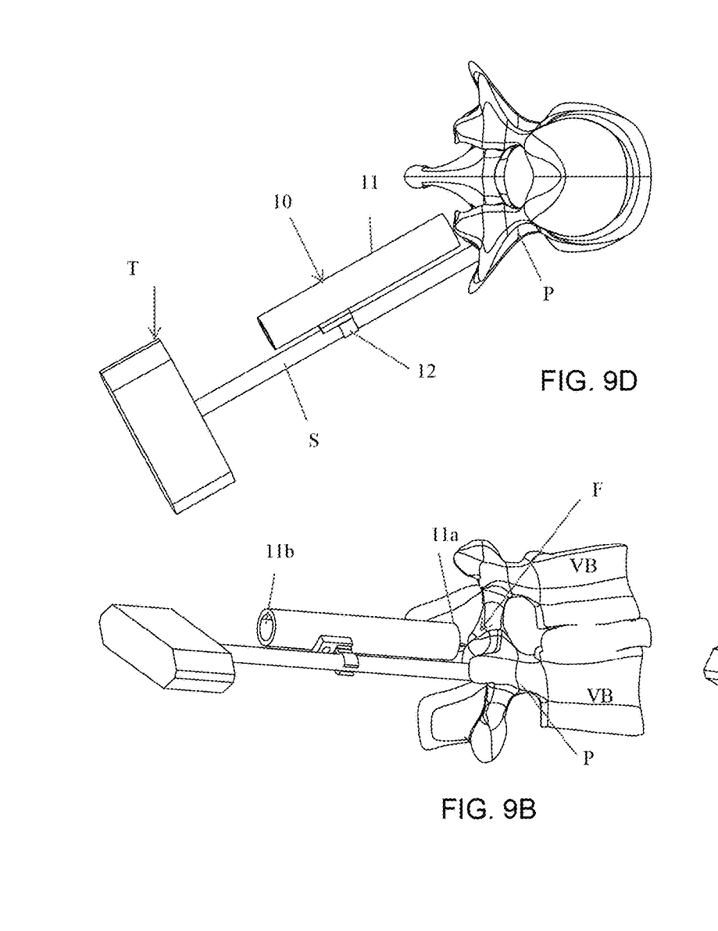
Figure 9C:
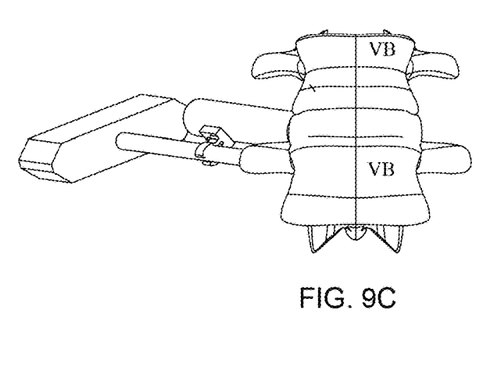
Figure 10A:
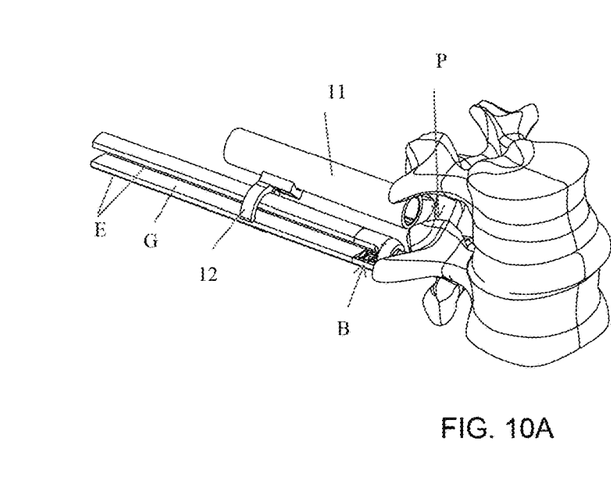
FIGS. 10A-10D are perspective, sagittal, coronal and axial views of the lumbar spinal segment with the tube assembly of FIG. 1 aligned over a facet joint and supported on a bone screw assembly.
Figure 10B:
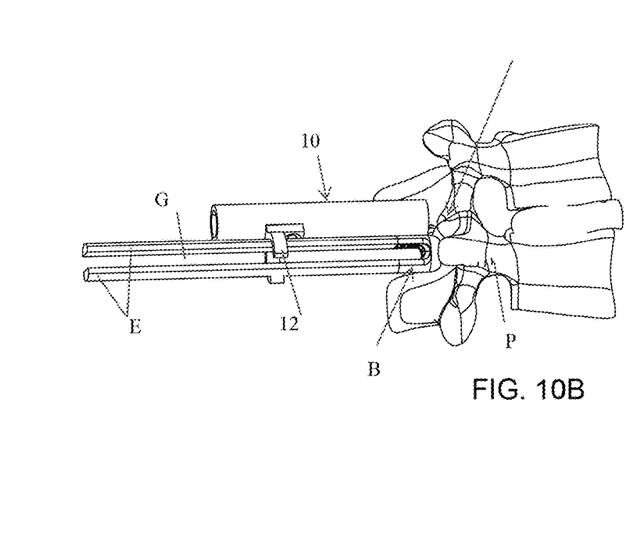
Figure 10C:
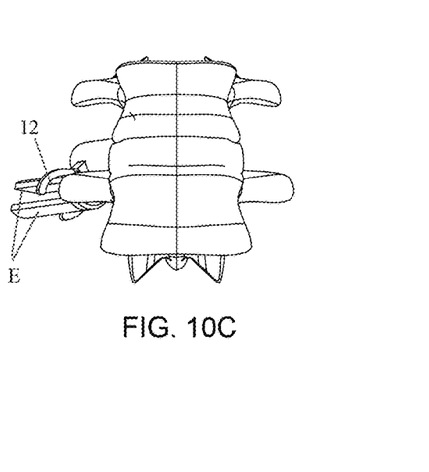
Figure 10D:
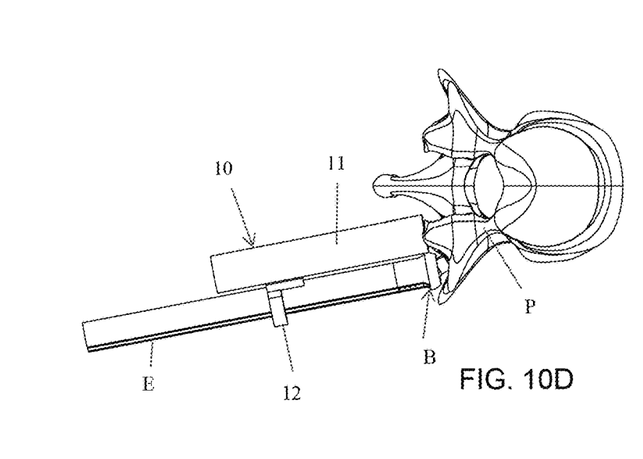

The facet fusion tube assembly 10 can also include an inner rod 15, as shown in FIGS. 5-8. The inner rod includes an elongated shank 15a terminating in an enlarged head 15b at one end and in a conical tip 15c at the opposite end. The shank 15a is sized to extend through the central bore 11c of the tube 11 with the head 15b in contact with the proximal end 11a of the tube and the conical tip 15c projecting beyond the distal end 11b, as best seen in FIGS. 7-8. It can be appreciated that the inner rod 15 is not used when the centering cap 14 is in position. The inner rod has a length from the distal end of the head 15b to the transition from the shank 15a to the conical tip 15c that is at least equal to the length of the tube 11, such as 80 mm in the illustrated embodiment. In this embodiment, the overall length of the rod from end-to-end is 105 mm, and the length of the conical tip is 5 mm. The inner rod 15 is thus sized in relation to the tube 11 so that the conical tip 15c projects beyond the distal end 11b of the tube, as shown in FIGS. 7-8. The enlarged head 14b can have a diameter greater than the outer diameter of the tube, such as 14 mm in a specific embodiment. The elongated shank 15a can have an outer diameter of 8.5 mm, which is slightly less than the 10 mm inner diameter of the bore 11c, thereby providing a close running fit.

Use of the facet fusion tube assembly 10 of the present disclosure is demonstrated with reference to FIGS. 9A-9D and 10A-10D. Each of these figures depicts a method for accessing the facet joint with the assembly 10 using an adjacent tool or instrument as an anchor element. In FIGS. 9A-9D, the anchor element is a tool T, such as a probe with an elongated shaft S extending into a bore in the pedicle P prepared to receive a bone screw. With the tool T in position, the tube assembly 10 can be introduced into the spine with the inner rod 15 in position, as shown in FIGS. 7-8. The inner rod helps navigate the distal end 11b of the tube through the surrounding soft tissue and prevents any tissue from creeping into the tube. Moreover, the conical tip 15c can dock with the facet joint by contact with the articular processes at the joint. Once the distal end 11b of the tube is properly positioned at the facet joint, the clip 12 can be engaged to the shaft S of the anchor element or tool T. Alternatively, the clip 12 can be engaged to an upper portion of the shaft S, and the clip and tube can slide down the shaft S until the distal end 11a of the tube is properly positioned. With the tube 11 in position, the inner rod can be removed. At this point, the tube 11 is aligned with the facet joint F so that the facet joint can be reliably accessed and prepared for fusion. The tube also provides a cannula for introduction of graft material into the facet joint. The inner rod 15 can be used to push the graft material through the tube 11. The clip 12 is configured to firmly engage the shaft S to hold the position of the tube assembly 10 as the minimally invasive surgical procedure continues.

It is also contemplated that with the tube assembly 10 oriented relative to the facet joint and the inner rod 15 removed, the centering cap 13 can be engaged to the proximal end 11a of the tube 11, in the manner shown in FIGS. 1-2. The centering cap can then be used to guide a working tool, such as a burring tool, used to prepare the facet joint to receive the graft material. The tube assembly 10 can remain engaged to the shaft S of the adjacent tool T during this step of the procedure to ensure that the burring tool is accurately and continuously aligned with the facet joint.

As shown in FIGS. 10A-10D, a bone screw assembly B with frangible extensions E may serve as the guide and anchor element for the tube assembly 10. With the bone screw assembly B engaged in the pedicle P, the extensions E project from the tulip head of the bone screw. The bone screw assembly B is preferably rotated so that the clip 12 spans the gap G between the extensions to ensure that the arms 12c (FIGS. 3A-3D) can adequately grasp the extensions to hold the tube 11 in a fixed position in line with the facet joint F. Once the facet procedure has been completed, the tube assembly 11 can be unclipped from the extensions E and the extensions severed from the tulip head of the bone screw assembly B.

It can be appreciated that the facet fusion tube assembly 10 of the present disclosure, and particularly the clip 12, can be configured to engage any elongated instrument or tool. Thus, rather than the probe T or bone screw assembly B, the tube assembly can be engaged to a working channel cannula that is anchored to the pedicle P adjacent the desired facet joint F. The clip 12, and particularly the base 12a, is sized so that the tube 11 will be automatically aligned with the facet joint when it is mounted to a tool or instrument that is engaged to the pedicle. The tube 11 will then provide a stable base for performing various steps in the facet fusion process—from preparing the facet joint using a bone burr, for instance, to introducing bone graft material, to packing the graft material into the prepared space using the inner rod.

The components of the facet fusion tube assembly 10 can be fabricated from the same material as the tools and instruments, such as stainless steel. However, since the components are not intended to be load-bearing, they can be formed of suitably rigid polymers. The components can be formed or a radiolucent or non-radiolucent material. The arms 12c of the clip 12 are preferably resilient so that the arms can be deflected outward relative to each other as the clip is engaged on the outer surface of a tool or instrument. The resilient nature of the arms will generate a clamping force that is sufficient to hold the position of the tube assembly 10 on the tool or instrument while the facet fusion procedure is conducted.

What is claimed is:

1. A method for preparing a facet joint at a vertebral level for fusion, comprising:
   introducing an elongated anchor element to a vertebral body adjacent the facet joint;
   providing a facet fusion tube assembly including a hollow elongated tube having a proximal end and a distal end and a resilient clip fastened to an outer surface of the elongated tube;
   extending an inner rod through the elongated tube with a tip of the inner rod extending beyond the distal end of the tube;
   introducing the elongated tube and the inner rod into the vertebral level laterally adjacent the anchor element with the tip of the inner rod extending beyond the distal end of the tube until the tip of the inner rod is in immediate proximity to or in contact with a portion of the facet joint;
   clamping the elongated tube to the anchor element using the resilient clip;
   removing the inner rod from the elongated tube with the elongated tube clamped to the anchor element; and
   introducing a tool or instrument into the hollow elongated tube to perform an operation on the facet joint,
   wherein the elongated tube is clamped to the anchor element as the elongated tube is introduced into the vertebral level.

2. The method of claim 1, wherein
   the resilient clip is fastened to an outer surface of the elongated tube, the resilient clip having a pair of opposing resilient arms extending outward from said outer surface and defining a cylindrical interior engagement surface adapted to engage the elongated anchor element, said pair of arms configured to resiliently deflect outward relative to each other for said clip to engage the elongated anchor element.

3. The method of claim 2, wherein:
   said resilient clip includes a base; and
   said hollow elongated tube and said base define fastener holes in alignment with each other to receive a fastener to removably fasten the clip to the hollow elongated tube.

4. The method of claim 2, wherein said resilient clip includes a base with said arms projecting from said base, said base defining a notch between said arms to facilitate outward deflection of said arms relative to each other.

5. The method of claim 2, wherein said inner rod has a conical tip adapted to guide the elongated tube through soft tissue when accessing the facet joint.

6. The method of claim 2, wherein said facet fusion tube assembly further includes a centering cap having an elongated cylindrical body sized for a press fit within said hollow elongated tube, said centering cap defining a centering bore.

7. The method of claim 6, wherein the proximal end of said hollow elongated tube and said cylindrical body define at least one nested ridge and channel interface to prevent relative rotation between said hollow elongated tube and said centering cap.

8. The method of claim 1, further comprising:
   after removing the inner rod, engaging a centering cap to the proximal end of the elongated tube, the centering cap defining a center opening in communication with the hollow elongated tube; and
   the step of introducing a tool or instrument includes extending the tool or instrument through the center opening of the centering cap, whereby the centering cap maintains the tool or instrument in a centered position.

9. A method for preparing a facet joint at a vertebral level for fusion, comprising:

introducing an elongated anchor element to a vertebral body adjacent the facet joint;

providing a facet fusion tube assembly including a hollow elongated tube having a proximal end and a distal end and a resilient clip fastened to an outer surface of the elongated tube;

extending an inner rod through the elongated tube with a tip of the inner rod extending beyond the distal end of the tube;

introducing the elongated tube and the inner rod into the vertebral level laterally adjacent the anchor element with the tip of the inner rod extending beyond the distal end of the tube until the tip of the inner rod is in immediate proximity to or in contact with a portion of the facet joint;

clamping the elongated tube to the anchor element using the resilient clip;

removing the inner rod from the elongated tube with the elongated tube clamped to the anchor element; and introducing a tool or instrument into the hollow elongated tube to perform an operation on the facet joint, wherein the elongated tube is clamped to the anchor element after the tip of the inner rod is in immediate proximity to or in contact with the portion of the facet joint.

10. The method of claim 9, further comprising:

after removing the inner rod, engaging a centering cap to the proximal end of the elongated tube, the centering cap defining a center opening in communication with the hollow elongated tube; and the step of introducing a tool or instrument includes extending the tool or instrument through the center opening of the centering cap, whereby the centering cap maintains the tool or instrument in a centered position.

11. The method of claim 9, wherein the resilient clip is fastened to an outer surface of the elongated tube, the resilient clip having a pair of opposing resilient arms extending outward from said outer surface and defining a cylindrical interior engagement surface adapted to engage the elongated anchor element, said pair of arms configured to resiliently deflect outward relative to each other for said clip to engage the elongated anchor element.

12. The method of claim 11, wherein:

said resilient clip includes a base; and said hollow elongated tube and said base define fastener holes in alignment with each other to receive a fastener to removably fasten the clip to the hollow elongated tube.

13. The method of claim 11, wherein said resilient clip includes a base with said arms projecting from said base, said base defining a notch between said arms to facilitate outward deflection of said arms relative to each other.

14. The method of claim 11, wherein said inner rod has a conical tip adapted to guide the elongated tube through soft tissue when accessing the facet joint.

15. The method of claim 11, wherein said facet fusion tube assembly further includes a centering cap having an elongated cylindrical body sized for a press fit within said hollow elongated tube, said centering cap defining a centering bore.

16. The method of claim 15, wherein the proximal end of said hollow elongated tube and said cylindrical body define at least one nested ridge and channel interface to prevent relative rotation between said hollow elongated tube and said centering cap.

* * * * *